(12) United States Patent
McLawhorn (10) Patent No.: US 10,244,921 B2
(45) Date of Patent: Apr. 2, 2019

(54) ENDOSCOPIC SYSTEM FOR RESECTION OF TISSUE

(75) Inventor: Tyler E. McLawhorn, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 680 days.

(21) Appl. No.: 13/205,803

(22) Filed: Aug. 9, 2011

(65) Prior Publication Data

US 2012/0041259 A1    Feb. 16, 2012

Related U.S. Application Data

(60) Provisional application No. 61/372,271, filed on Aug. 10, 2010.

(51) Int. Cl.
*A61B 1/018* (2006.01)
*A61B 17/32* (2006.01)
*A61B 1/00* (2006.01)

(52) U.S. Cl.
CPC ........ *A61B 1/00087* (2013.01); *A61B 1/0014* (2013.01); *A61B 1/00071* (2013.01);
(Continued)

(58) Field of Classification Search
CPC .. A61B 1/04–1/05; A61B 1/012; A61B 1/015; A61B 1/018; A61B 1/00087;
(Continued)

(56) References Cited

U.S. PATENT DOCUMENTS

| 2,708,437 A | 5/1955 | Hutchins |
| 4,368,734 A * | 1/1983 | Banko ................ A61F 9/00763 606/107 |

(Continued)

FOREIGN PATENT DOCUMENTS

| JP | 2001-513355 | 9/2001 |
| JP | 2005-58343 | 3/2005 |
| WO | WO99/07295 | 2/1999 |

OTHER PUBLICATIONS

International Search Report and Written Opinion for PCT/US2011/046917 dated Dec. 5, 2011, 13 pgs.

(Continued)

*Primary Examiner* — John P Leubecker
(74) *Attorney, Agent, or Firm* — Brinks Gilson & Lione (57) ABSTRACT

The present embodiments provide apparatus for facilitating endoscopic resection of tissue. The apparatus comprises proximal and distal barrels. The proximal barrel is adapted to be coupled to an endoscope. A cutting member is disposed within a lumen of the distal barrel and configured to resect a segment of tissue. In one embodiment, a central longitudinal axis of the proximal barrel is radially offset from a central longitudinal axis of the distal barrel, thereby allowing the cutting member to be centered relative to the working lumen of the endoscope. Additionally, the cutting member may comprise at least one viewing window that permits endoscopic visualization of tissue distal to the distal barrel when the cutting member is disposed within the distal barrel.

18 Claims, 5 Drawing Sheets

(52) U.S. Cl.
CPC ...... *A61B 1/00089* (2013.01); *A61B 1/00101* (2013.01); *A61B 1/018* (2013.01); *A61B 2017/32004* (2013.01); *A61B 2017/320024* (2013.01)

(58) Field of Classification Search
CPC ............ A61B 1/00089; A61B 1/00101; A61B 1/00135; A61B 1/0014; A61B 17/320016; A61B 2017/0034; A61B 2017/320024; A61B 2017/32004
USPC ........ 600/127, 129, 125; 606/114, 170, 184, 606/175, 167
See application file for complete search history.

(56) References Cited

U.S. PATENT DOCUMENTS

| | | | | |
|---|---|---|---|---|
| 5,395,030 | A * | 3/1995 | Kuramoto et al. | 227/179.1 |
| 5,976,073 | A * | 11/1999 | Ouchi | A61B 1/00089 600/129 |
| 6,039,748 | A * | 3/2000 | Savage | A61B 17/32002 606/107 |
| 6,142,931 | A * | 11/2000 | Kaji | A61B 1/31 600/102 |
| 6,203,559 | B1 * | 3/2001 | Davis et al. | 606/198 |
| 8,469,880 | B2 * | 6/2013 | Herrmann et al. | 600/156 |
| 2001/0053909 | A1 * | 12/2001 | Nakada | A61B 1/00089 606/47 |
| 2003/0171651 | A1 * | 9/2003 | Page | A61B 17/0469 600/127 |
| 2003/0191413 | A1 * | 10/2003 | Damarati | A61B 10/0266 600/567 |
| 2005/0033115 | A1 | 2/2005 | Okada | |
| 2005/0070890 | A1 * | 3/2005 | Nobis | A61B 17/32001 606/45 |
| 2005/0090709 | A1 * | 4/2005 | Okada | A61B 1/0005 600/104 |
| 2007/0066870 | A1 * | 3/2007 | Ohashi | A61B 1/00089 600/127 |
| 2007/0135803 | A1 * | 6/2007 | Belson | 606/1 |
| 2007/0197862 | A1 * | 8/2007 | Deviere | A61B 1/00087 600/102 |
| 2008/0103410 | A1 * | 5/2008 | Karpiel | A61B 1/00089 600/564 |
| 2009/0198212 | A1 * | 8/2009 | Timberlake | A61B 1/018 604/506 |
| 2009/0242612 | A1 | 10/2009 | Adams et al. | |
| 2009/0270897 | A1 * | 10/2009 | Adams | A61B 1/303 606/170 |
| 2010/0016659 | A1 * | 1/2010 | Weitzner | A61B 1/00073 600/104 |
| 2010/0125164 | A1 * | 5/2010 | LaBombard | 600/104 |
| 2010/0191052 | A1 * | 7/2010 | Surti | A61B 1/00087 600/106 |

OTHER PUBLICATIONS

International Preliminary Report on Patentability for PCT/US2011/046917 dated Feb. 12, 2013, 9 pgs.
Patent Examination Report No. 1 for Australian Patent Application 2011289600 dated May 30, 2013, 3 pgs.
Communication Pursuant to Rules 161(1) and 162 EPC for European Patent Application 11743755.8 dated Mar. 19, 2013, 2 pgs.
Response to Communication Pursuant to Rules 161(1) and 162 EPC for European Patent Application 11743755.8 filed Sep. 17, 2013, 8 pgs.
Response to Patent Examination Report No. 1 for Australian Patent Application 2011289600 filed May 5, 2014, 16 pgs.
Notice of Acceptance for Australian Patent Application 2011289600 dated Jun. 25, 2014, 2 pgs.
Office Action for Japanese Patent Application 2013-524144 dated Mar. 11, 2014, 7 pgs. including English translation.
Response to Office Action for Japanese Patent Application 2013-524144 filed Jun. 11, 2014, 3 pgs. English translation only.
Decision for Patent for Japanese Patent Application 2013-524144 dated Oct. 28, 2014, 4 pgs. including English translation.
Examination Report for EP11743755.8 dated Aug. 2, 2018, 5 pgs.

* cited by examiner

ENDOSCOPIC SYSTEM FOR RESECTION OF TISSUE

PRIORITY CLAIM

This invention claims the benefit of priority of U.S. Provisional Application Ser. No. 61/372,271, entitled "Endoscopic System For Resection Of Tissue," filed Aug. 10, 2010, the disclosure of which is hereby incorporated by reference in its entirety.

BACKGROUND INFORMATION

The present invention relates generally to the field of medical devices, and more particularly, to an endoscopic system for resection of tissue.

There are various instances in which it may become necessary or desirable to resect a segment of a patient's tissue, for example, to obtain tissue samples or remove potentially harmful or cancerous localized tissue segments. At the present time, partial or full thickness resection of tissue is often left for open surgical procedures, resulting in the drawbacks associated with open surgery such as increased invasiveness and potentially longer recovery times.

There are some endoscopic techniques for cutting and collecting tissue. For example, one or more cutting instruments, such as a needle knife, may be advanced through a working lumen of an endoscope. The cutting instrument then may be advanced beyond the distal end of the endoscope and actuated by supplying an electrical current to the tip of the instrument. Once heated, the cutting instrument may be positioned to engage and cut the target tissue. The tissue then may be captured and removed, for example, by using a forceps advanced through the working lumen of the endoscope.

When cutting instruments, such as needle knives, are used in the above-described manner, the result may yield an imprecise cutting of tissue. In particular, when a sharp, pointed and/or heated instrument is advanced distal to the endoscope, a risk exists of improperly maneuvering the cutting instrument and therefore inadvertently cauterizing or searing healthy or non-target tissue. Further, in these procedures, the extended cutting instrument is generally moved in a circular motion, which may increase the risk of incision to the unrelated tissue.

Other instruments, such as needles, may be advanced through a lumen of an endoscope and may engage tissue. For example, a biopsy needle may be used to obtain a sample of tissue. However, the size of the needle is limited by the diameter of the working lumen of the endoscope, and therefore, the needle cannot resect a large segment of tissue.

There is a need for a safe and effective system for the resection of a wide range and size of tissue segments during endoscopic procedures.

SUMMARY

The present embodiments provide apparatus for facilitating endoscopic resection of tissue. The apparatus comprises proximal and distal barrels. The proximal barrel is adapted to be coupled to an endoscope. A cutting member is disposed within a lumen of the distal barrel and configured to resect a segment of tissue.

In one embodiment, a central longitudinal axis of the proximal barrel is radially offset from a central longitudinal axis of the distal barrel, thereby allowing the cutting member and the distal barrel to be centered relative to a working lumen of the endoscope. The cutting member may be coupled to an actuating member disposed within the working lumen of the endoscope, such that the actuating member is coupled to the cutting member along the central longitudinal axis of the distal barrel. Advantageously, the cutting member may be centered relative to the working lumen of the endoscope, such that when the actuating member is advanced and/or rotated, an enhanced and centered rotation of the cutting member may be achieved.

The cutting member may comprise a cylindrical main body having a beveled distal region. A stop member may be provided to limit maximum distal movement of the cutting member.

Additionally, the cutting member may comprise at least one viewing window. For example, a proximal support section of the cutting member may comprise a plurality of supporting struts separated by a plurality of viewing windows. Advantageously, the plurality of viewing windows permit endoscopic visualization of tissue distal to the distal barrel when the cutting member is disposed within the distal barrel.

A first separating segment formed between the proximal barrel and the distal barrel may prevent the distal barrel from being advanced proximally over the endoscope. A second separating segment formed between the proximal barrel and the distal barrel may limit proximal movement of the cutting member.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figures 1A, 1B:
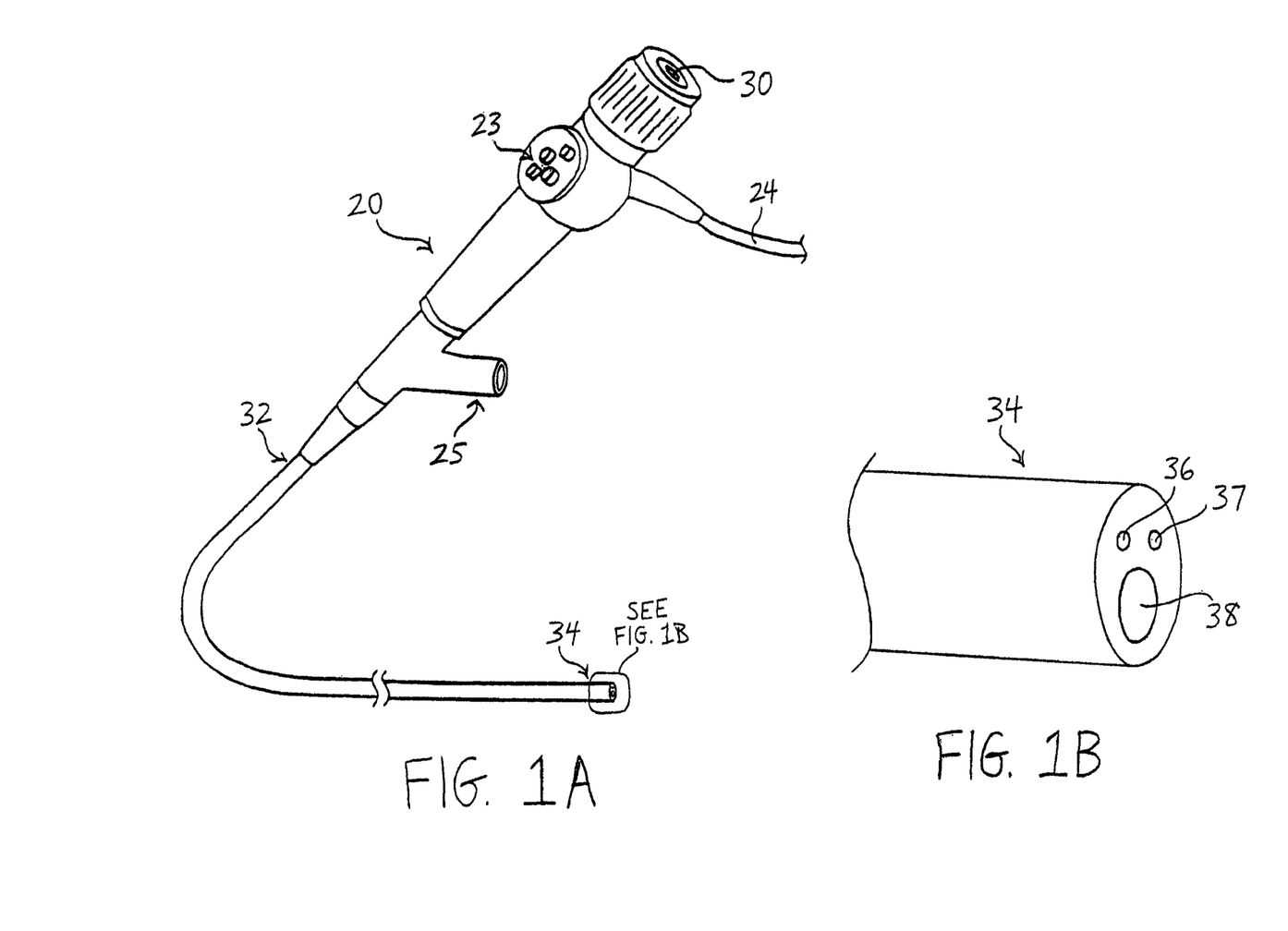
FIGS. 1A-1B are, respectively, a perspective view of an exemplary end-viewing endoscope and a close-up view of the distal region of the endoscope.

Referring now to FIGS. 1A-1B, an exemplary endoscope 20 is described, which may be used in conjunction with the tissue resection system described below. In FIG. 1A, the exemplary endoscope 20 comprises an end-viewing endoscope of known construction and having proximal and distal regions 32 and 34, respectively. The endoscope 20 may comprise fiber optic components 36 and 37 for illuminating and capturing an image distal to the endoscope 20, as depicted in FIG. 1B. A physician may view the images distal to the endoscope 20 using an eyepiece 30. A fiber optic cable 24 may be coupled between the endoscope 20 and a suitable light source. A control section 23 may be provided to maneuver the distal region 34 of the endoscope 20, and facilitate actuation of various components associated with the endoscope 20.

The endoscope 20 also may comprise a working lumen 38, as shown in FIG. 1B. An auxiliary port 25 may be placed in fluid communication with the working lumen 38, such that components advanced through the auxiliary port 25 are directed into the working lumen 38. The working lumen 38 may be sized to accommodate an array of medical components, such as a catheter, forceps, snare and the like. While one working lumen 38 is shown, additional lumens may be employed. Other features and components of the endoscope 20, and variations thereof, are generally known to those skilled in the art and are not critical to the present invention.

In a conventional procedure, the endoscope 20 may be advanced through a natural bodily lumen, such as the alimentary canal, to a position proximate a target location. A catheter or other medical device then may be advanced through the working lumen 38 of the endoscope 20 to the target location. Optionally, a needle or other suitable device may be used to puncture through an organ or a gastrointestinal wall to provide translumenal endoscopic access to various additional bodily regions.

Referring now to FIGS. 2-7, a first embodiment of an endoscopic tissue resection system 50 is described. In this embodiment, the endoscopic tissue resection system 50 generally comprises a proximal barrel 60 and a distal barrel 80. As explained in further detail below, the proximal barrel 60 may be coupled to the distal region 34 of the endoscope 20, while a cutting member 100 may be disposed within the distal barrel 80. The cutting member 100 may be coupled to an actuating member 115, and may be selectively longitudinally advanced and/or rotated with respect to the distal barrel 80 to resect tissue.

Figures 4, 5:
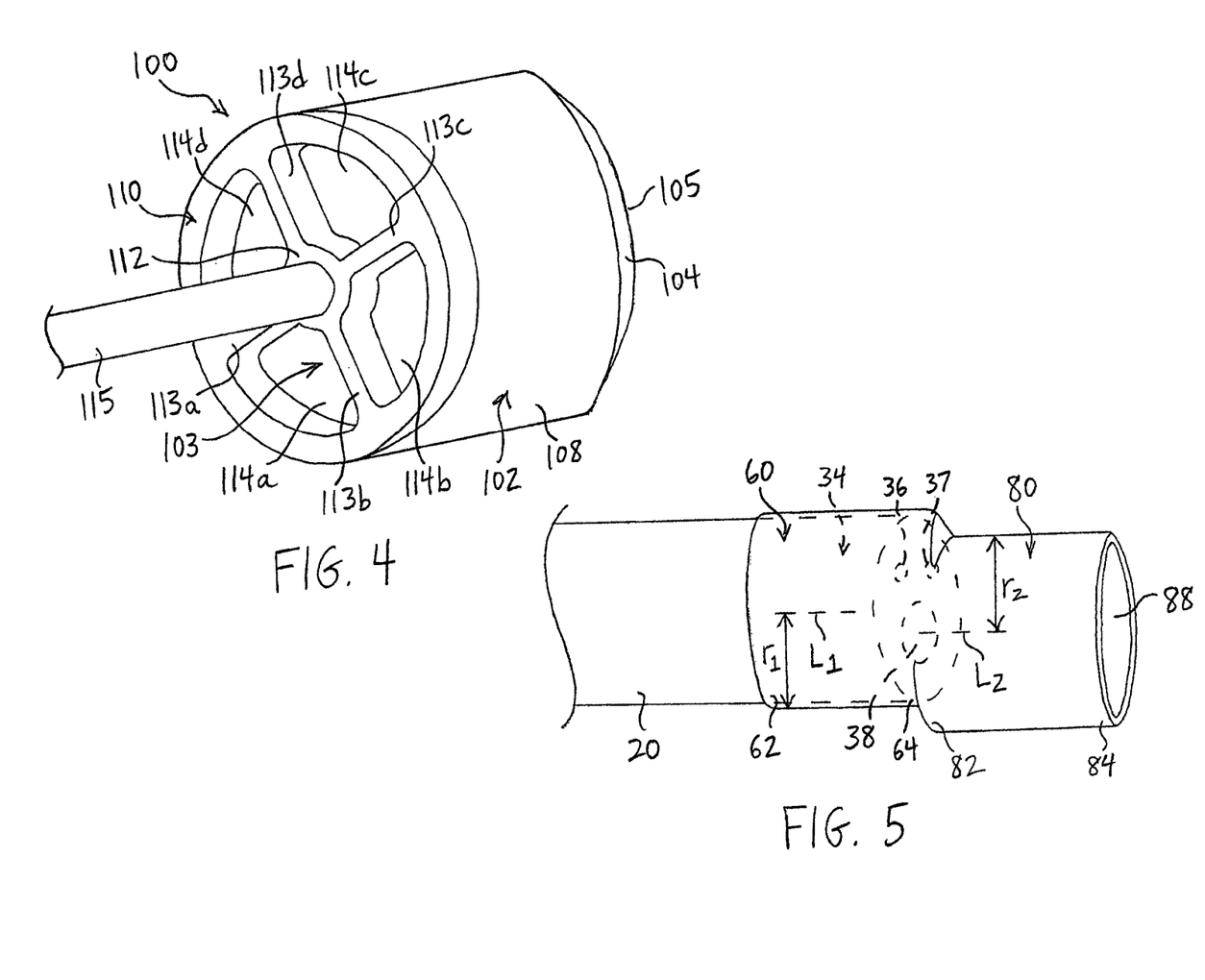
FIG. 4 is an isolated perspective view of a cutting member and an actuating member of the endoscopic tissue resection system of FIGS. 2-3.
FIG. 5 is a perspective view showing the endoscopic tissue resection system of FIGS. 2-3 being coupled to the distal region of the endoscope of FIGS. 1A-1B.

The proximal barrel 60 comprises proximal and distal regions 62 and 64, respectively, and a lumen 68 extending therebetween. The proximal region 62 may be coupled to the distal region 34 of the endoscope 20. Preferably, at least a portion of the proximal region 62 of the proximal barrel 60 is disposed about an exterior surface of the endoscope 20, as shown in FIG. 5. In the embodiment shown, most of the proximal barrel 60, spanning between the proximal and distal ends 62 and 64, is disposed about the exterior surface of the endoscope 20, although any portion may be coupled to the endoscope 20 so long as a secure attachment is achieved.

In one embodiment, at least a portion of the proximal region 62 comprises an elastic member having a first inner diameter in a relaxed state, and a second, slightly larger inner diameter when in an expanded state. If the proximal region 62 is elastic, it may be sized such that its inner diameter in the relaxed state is slightly smaller than an exterior diameter of the endoscope 20, but its inner diameter in the expanded state is slightly larger than the exterior diameter of the endoscope 20. This configuration allows at least the proximal region 62 of the proximal barrel 60 to elastically expand to be disposed over the distal region 34 of the endoscope 20. Once in place, the proximal region 62 will be allowed to return to its relaxed state, thereby securely engaging the proximal barrel 60 around the exterior surface of the endoscope 20 using a frictional fit, as shown in FIG. 5. An interior surface of the proximal portion 62 may comprise a texture or material, such as rubber, configured to increase the frictional fit with the exterior surface of the endoscope 20.

If desired, a securing means may be applied to secure a portion of the proximal barrel 60 directly to an exterior surface of the endoscope 20 to prohibit movement of the proximal barrel 60 with respect to the endoscope 20. For example, the securing means may comprise an adhesive tape, heat-shrink tubing, one or more tie-down bands, cable-ties, and the like. The securing means may be configured and disposed so as to not interfere with movement of the endoscope 20 through the patient. Further details of an exemplary securing means and techniques for securing a component, such as the proximal barrel 60, to an exterior surface of an endoscope are explained in U.S. Pat. Pub. No. 2007/0270897, the disclosure of which is hereby incorporated by reference in its entirety.

Figures 2, 3:
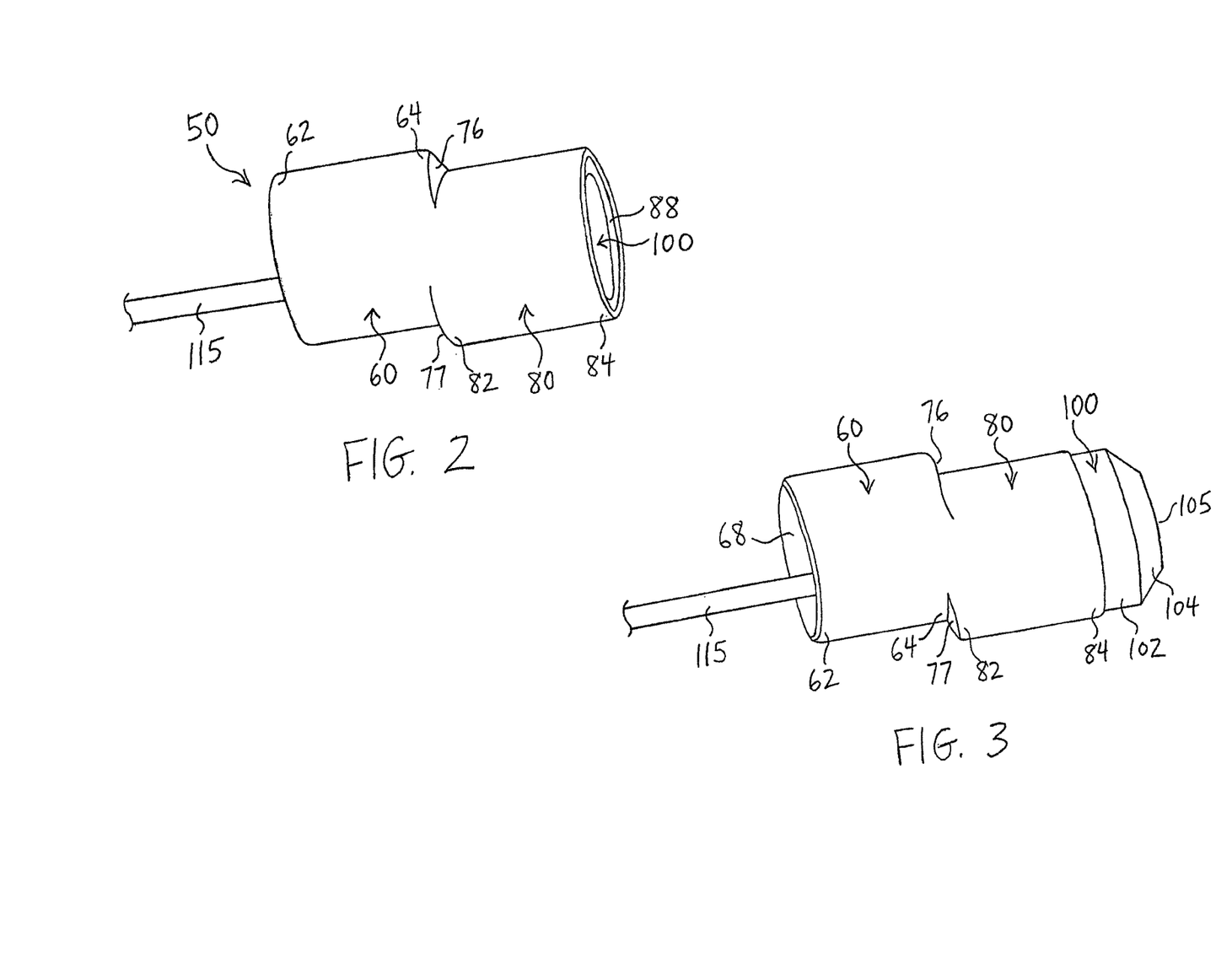
FIG. 2 is an elevated front perspective view of an endoscopic tissue resection system with a cutting member in a retracted state.
FIG. 3 is a rear perspective view of the endoscopic tissue resection system of FIG. 2 with the cutting member in an advanced state.

The distal barrel 80 comprises proximal and distal regions 82 and 84, respectively, and a lumen 88 extending therebetween. The proximal region 82 of the distal barrel 80 may be coupled to the distal region 64 of the proximal barrel 60, as shown in FIGS. 2-3. The proximal and distal barrels 60 and 80 may be formed integrally, or may comprise two distinct sections that are coupled together at first and second separating segments 76 and 77. If two distinct sections are used, the proximal and distal barrels 60 and 80 may comprise different materials and/or flexibilities. For example, the proximal barrel 60 may be at least partially formed from an elastic material to engage around the exterior surface of the endoscope 20 as noted above, while the distal barrel 80 may be formed from a more rigid material that does not bend or flex when the cutting member 100 is advanced or rotated therein, as explained further below.

In accordance with one aspect, the distal barrel 80 is radially offset from the proximal barrel 60. In particular, the proximal barrel 60 comprises a central longitudinal axis $L_1$, while the distal barrel 60 comprises a central longitudinal axis $L_2$, whereby the central longitudinal axes $L_1$ and $L_2$ are not radially aligned, as shown in FIG. 5. Notably, the working lumen 38 of the endoscope 20 is not radially centered within the endoscope 20, as is the case for most endoscope designs. Since the working lumen 38 is not centered within the endoscope 20, the radial offset between central longitudinal axes $L_1$ and $L_2$ allows the proximal barrel 60 to be aligned with the exterior surface of the endoscope 20 along the central longitudinal axes $L_1$, and further allows the distal barrel 80 to be aligned with the working lumen 38 along the central longitudinal axes $L_2$, as shown in FIG. 5. Advantageously, the cutting member 100, when disposed within the distal barrel 80, is centered relative to the working lumen 38. Further, when the actuating member 115 that is coupled to the cutting member 100 is disposed within the working lumen 38, an enhanced, centered rotation of the cutting member 100 within the distal barrel 80 may be achieved, as explained further below.

A radius $r_1$ is formed between the central longitudinal axis $L_1$ of the proximal barrel 60 and an exterior surface of the proximal barrel 60, as shown in FIG. 5. Further, a radius $r_2$ is formed between the central longitudinal axis $L_2$ of the distal barrel 80 and an exterior surface of the distal barrel 80. In the embodiment shown, the radii $r_1$ and $r_2$ are identical or approximately identical. However, the radius $r_2$ may be larger or smaller than radius $r_1$, depending on the diameter of the cutting instrument 100 that is desired as dictated, for example, by the particular size of tissue to be resected. Accordingly, the relative diameters of the proximal and distal barrels 60 and 80 need not be identical, but rather may vary depending on both the outer diameter of the endoscope 20 and the diameter of the cutting instrument 100.

Figure 6:
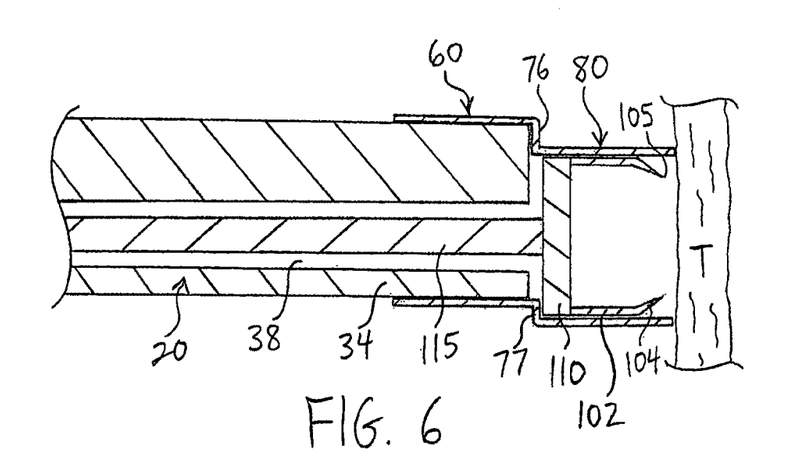
FIGS. 6-7 are side-sectional views of the endoscopic tissue resection system of FIGS. 2-3 with the cutting member in retracted state and advanced states, respectively.
Figure 7:
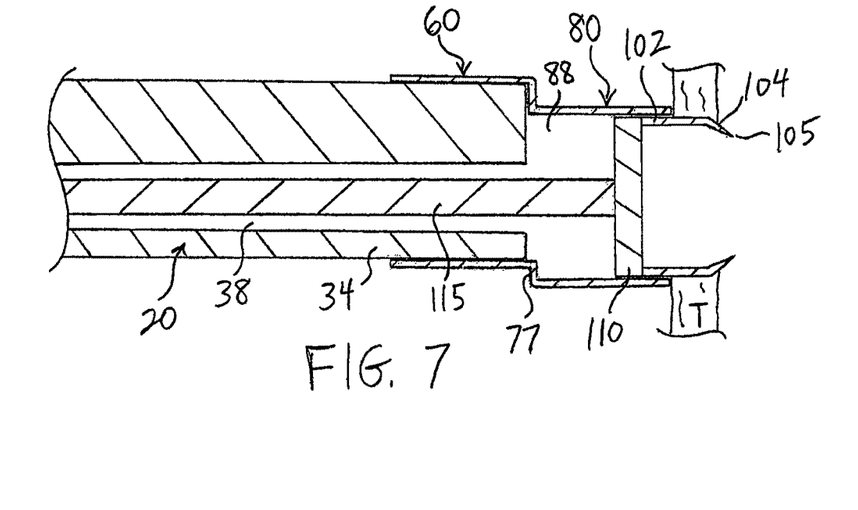

Referring to FIG. 4, an exemplary cutting member 100 is shown in isolation. The cutting member 100 comprises a cylindrical main body 102 having a beveled distal region 104. The main body 102 is generally hollow and comprises a lumen 103 formed therein. The beveled distal region 104 terminates in a sharpened distal tip 105, as shown in FIGS. 4 and 6-7. The main body 102 preferably comprises a cylindrical exterior surface 108 having an outer diameter that is just smaller than an inner diameter of the distal barrel 80. Therefore, the main body 102 and the beveled distal region 104 of the cutting member 100 may be longitudinally and rotationally disposed within the lumen 88 of the distal barrel 80, as shown in FIGS. 6-7.

In one embodiment, the main body 102 of the cutting member 100 is coupled to the actuating member 115 by a proximal support section 110. The proximal support section 110 preferably comprises an outer diameter identical to the main body 102, as shown in FIG. 4, and therefore may be longitudinally and rotationally disposed within the lumen 88 of the distal barrel 80 along with the main body 102, as shown in FIGS. 6-7. The proximal support section 110 further comprises a central hub 112 and a plurality of supporting struts 113a-113d extending radially outward from the central hub 112. The actuating member 115 is securely attached to the central hub 112, e.g., using a friction fit, suitable mechanical means, adhesive, solder, weld, or other suitable means.

The plurality of supporting struts 113a-113d are separated by a plurality of viewing windows 114a-114d, as shown in FIG. 4. Advantageously, the plurality of supporting struts 113a-113d provide support to the main body 102, while the plurality of viewing windows 114a-114d permit endoscopic visualization of tissue distal to the distal barrel 80 when the cutting member 100 is disposed within the distal barrel 80, as shown in FIGS. 6-7. While four supporting struts 113a-113d and four viewing windows 114a-114d are shown, it will be apparent that greater or fewer struts and windows may be provided.

Referring to FIGS. 6-7, an exemplary use of the endoscopic tissue resection system 50 is described to resect tissue T in a safe and effective manner. In a first step, the endoscope 20 may be retrofitted using the tissue resection system 50 by securing at least a portion of the proximal barrel 60 to the endoscope 20. For example, the proximal portion 62 may be disposed over the distal region 34 of the endoscope 20 and secured using elastic properties of the proximal portion 62 and/or an external securing means, as explained above. Notably, the first separating segment 76 formed between the proximal barrel 60 and the distal barrel 80 forms a step to prevent the distal barrel 80 from being advanced proximally over the endoscope 20, as depicted in FIG. 6.

The cutting member 100 is disposed within the lumen 88 of the distal barrel 80, and is disposed for longitudinal and rotational movement relative to the distal barrel 80. The second separating segment 77 formed between the proximal barrel 60 and the distal barrel 80 forms a step to prevent proximal movement of the cutting member 100 outside of the distal barrel 80, as depicted in FIG. 6.

The cutting member 100 is disposed within the lumen 88 of the distal barrel 80 in a retracted state, as shown in FIG. 6, where the sharpened distal tip 105 of the cutting member 100 is confined within the distal barrel 80, i.e., the sharpened distal tip 105 is not exposed and cannot inadvertently cut tissue. At this time, the proximal support section 110 of the cutting member 100 may abut the second separating segment 77. The actuating member 115 extends proximally from the proximal support section 110, through the working lumen 38, and through the auxiliary port 25 of the endoscope 20 for manipulation by a user.

The endoscope 20 may be advanced to a desired target site using suitable imaging techniques, such as the fiber optic components 36 and 37, an ultrasound transducer, fluoroscopic techniques in conjunction with radiopaque bands, and the like. Once the physician has properly positioned the device adjacent to the tissue T to be resected, a proximal end of the actuating member 115 is actuated to cause distal advancement and/or rotation of the main body 102 and the beveled distal region 104 relative to the distal barrel 80. The actuating member 115 may comprise a torque cable or another suitable elongated member. The actuating member 115 may be manipulated manually, or alternatively, the proximal end of the actuating member 115 may be coupled to an electric motor, such as a drill, to facilitate controlled actuation of the cutting member 100, e.g., at the desired revolutions per minute (rpm).

The sharpened distal tip 105 engages and resects the selected portion of the tissue T, as shown in FIG. 7. When the desired amount of tissue T is resected and held within the lumen 103 of the main body 102 of the cutting member 100, the actuating member 115 may be proximally retracted such that the cutting member 100 assumes the retracted state shown in FIG. 6 for removal from the patient. The tissue resected has been collected and may be evaluated upon removal of the endoscope 20.

Advantageously, the plurality of viewing windows 114a-114d permit endoscopic visualization of the tissue T being resected by the cutting member 100 during the process. Further, since the main body 102 of the cutting member 100 is centered relative to the working lumen 38, an enhanced, centered rotation of the cutting member 100 may be achieved. Additionally, the system 50 provides a simple endoscopic tissue resection system that may be used as a retrofit to an existing endoscope 20.

Figure 8:
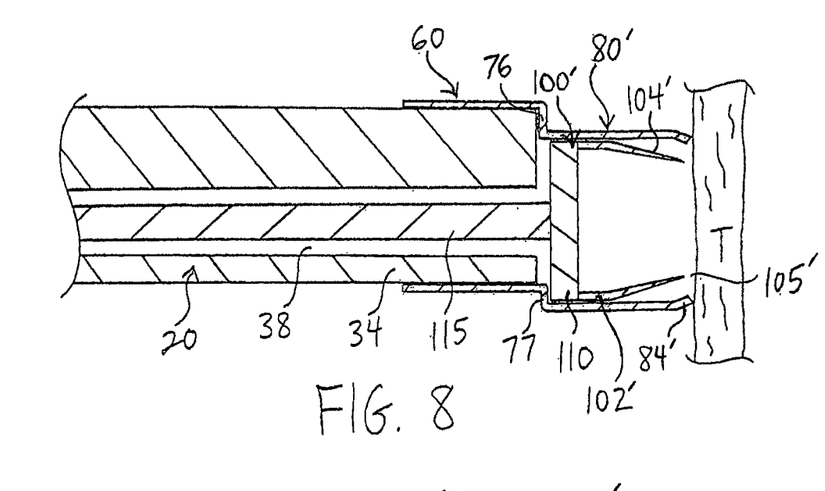
FIGS. 8-9 are side-sectional views of an alternative endoscopic tissue resection with a cutting member in retracted state and advanced states, respectively.
Figure 9:
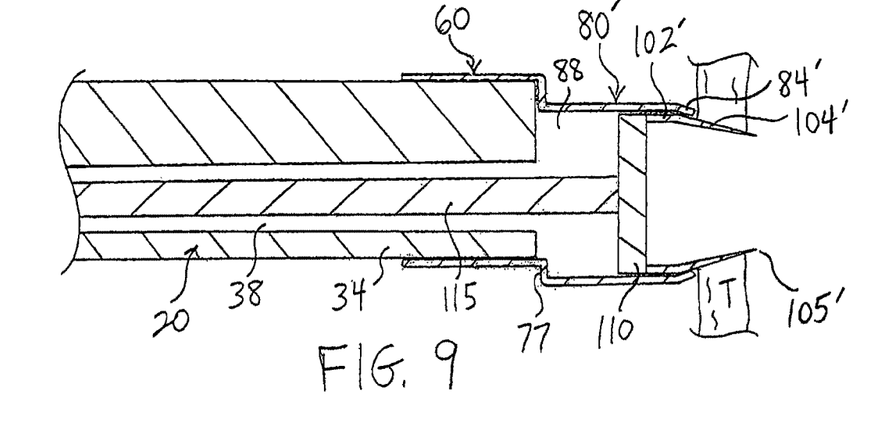

In an alternative embodiment, shown in FIGS. 8-9, a distal barrel 80' includes a stop member 84' configured to limit distal movement of an alternative cutting member 100'. In this example, the stop member 84' is formed as an inward taper at the distal end of the distal barrel 80'. As shown in FIGS. 8-9, the stop member 84' may cooperate with a portion of the beveled distal portion 104' of the cutting member 100' to inhibit further distal advancement of the cutting member 100', thereby ensuring that the proximal support section 110 and/or the main body 102' of the cutting member 100' remain inside of the distal barrel 80'. However, the sharpened distal tip 105' is allowed to extend distal to the distal barrel 80' to achieve a resection of tissue. Notably, in this embodiment, the cutting member 100' may comprise a shorter main body 102' and a longer beveled distal portion 104' to enable advancement within the distal barrel 80' as shown in FIG. 9. As an advantage, in the embodiment of FIGS. 8-9, the inward taper of the stop member 84' may facilitate a less traumatic entry of the endoscope 20 into a patient. While one exemplary stop member 84' has been shown, other stop members may be provided to control the advancement of the cutting member.

The proximal and distal barrels 60 and 80 may be used in endoscopic applications other than resection of tissue. Further, instruments other than the cutting member 100 may be used in conjunction with the proximal and distal barrels 60 and 80, for example, where it is desirable to center any instrument within a barrel and relative to the working lumen 38 of the endoscope 20. Further, the proximal and distal barrels 60 and 80 provided in accordance with the present embodiments may be used in conjunction with an array of existing commercial endoscopes.

Further, various techniques may be used to ensure an atraumatic transition between the proximal and distal barrels 60 and 80. For example, the first separating segment 76 may be tapered at an angle to avoid a relatively steep step and to promote a smooth transition between the proximal and distal barrels 60 and 80. Additionally, the distal end 84 of the distal barrel 80 may comprise atraumatic features to promote a smooth insertion towards a target site.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. Apparatus for facilitating resection of tissue, the apparatus comprising:
   a proximal barrel adapted to be detachably coupled to a functional endoscope;
   a distal barrel coupled to the proximal barrel, the distal and proximal barrels each having a lumen partially overlapping with the lumen of the other, wherein the distal barrel comprises an outer circumferential region forming a substantially circular shape; and
   a cutting member disposed within a lumen of the distal barrel and configured to resect a segment of tissue,
   wherein a central longitudinal axis of the proximal barrel is radially offset from a central longitudinal axis of the distal barrel, and
   wherein the central longitudinal axis of the distal barrel is radially aligned with a working lumen of the endoscope.

2. The apparatus of claim 1 wherein the cutting member comprises a cylindrical main body having a beveled distal region.

3. The apparatus of claim 1 wherein the cutting member is disposed for longitudinal and rotational movement relative to the distal barrel.

4. The apparatus of claim 1 further comprising a stop member adapted to limit maximum distal movement of the cutting member.

5. The apparatus of claim 1 wherein the cutting member is coupled to an actuating member disposed within the working lumen of the endoscope, wherein the actuating member is coupled to a proximal support section of the cutting member along a central longitudinal axis of the distal barrel.

6. The apparatus of claim 1 wherein a proximal support section of the cutting member comprises a plurality of supporting struts separated by a plurality of viewing windows, wherein the plurality of viewing windows permit endoscopic visualization of tissue distal to the distal barrel.

7. The apparatus of claim 1 further comprising:
   a first separating segment formed between the proximal barrel and the distal barrel, wherein the first separating segment prevents the distal barrel from being advanced proximally over the endoscope; and
   a second separating segment formed between the proximal barrel and the distal barrel, wherein the second separating segment limits proximal movement of the cutting member.

8. The apparatus of claim 1 wherein at least a portion of the proximal barrel is adapted to be disposed about an exterior surface of the endoscope and comprises an elastic member having a larger diameter state adapted to be placed over the endoscope and a smaller diameter state that permits the proximal barrel to be elastically secured about the exterior surface of the endoscope.

9. The apparatus of claim 1 further comprising an endoscope, wherein the proximal barrel is disposed on a distal end of the endoscope.

10. A method for facilitating resection of tissue, the method comprising:
    providing apparatus comprising a proximal barrel and a distal barrel, the distal and proximal barrels each having a lumen partially overlapping with the lumen of the other;
    detachably coupling at least a portion of the proximal barrel to a functional endoscope;
    disposing a cutting member within a lumen of the distal barrel; and
    actuating the cutting member in at least one of a longitudinal or rotational direction relative to the distal barrel to resect a segment of tissue,
    wherein a central longitudinal axis of the cutting member is radially aligned with a central longitudinal axis of the distal barrel.

11. The method of claim 10 wherein a central longitudinal axis of the proximal barrel is radially offset from the central longitudinal axis of the distal barrel, wherein the central longitudinal axis of the distal barrel is aligned with a working lumen of the endoscope.

12. The method of claim 10 wherein the cutting member comprises a cylindrical main body and a beveled distal region, the method further comprising longitudinally advancing and rotating the cutting member relative to the distal barrel.

13. The method of claim 10 further comprising providing a stop member to limit maximum distal movement of the cutting member.

14. The method of claim 10 wherein the cutting member comprises at least one viewing window that permits endoscopic visualization of tissue distal to the distal barrel.

15. Apparatus for facilitating resection of tissue, the apparatus comprising:
    a proximal barrel adapted to be coupled to an endoscope;
    a distal barrel coupled to the proximal barrel; and
    a cutting member disposed within a lumen of the distal barrel and configured to resect a segment of tissue, wherein the cutting member is disposed for at least one of longitudinal and rotational movement relative to the distal barrel, wherein the cutting member comprises at least one viewing window that permits endoscopic visualization of tissue distal to the distal barrel,
wherein a central longitudinal axis of the proximal barrel is radially offset from a central longitudinal axis of the distal barrel, and wherein the central longitudinal axis of the distal barrel is radially aligned with a working lumen of the endoscope.

16. The apparatus of claim 15 wherein the cutting member comprises a cylindrical main body having a beveled distal region.

17. The apparatus of claim 15 wherein the cutting member is coupled to an actuating member disposed within the working lumen of the endoscope, wherein the actuating member is coupled to a proximal support section of the cutting member along the central longitudinal axis of the distal barrel.

18. The apparatus of claim 15 further comprising a stop member adapted to limit maximum distal movement of the cutting member.

* * * * *